United States Patent [19]

Kessler et al.

[11] Patent Number: 5,182,214
[45] Date of Patent: Jan. 26, 1993

[54] METHOD FOR DETECTION AND DETERMINATION OF HUMAN SERUM ALBUMIN

[76] Inventors: Manfred Kessler, Lorenz-Vest-Weg 11, 8041 Graz; Otto S. Wolfbeis, Im Hoffeld 32, 8046 Graz, both of Austria

[21] Appl. No.: 556,268
[22] Filed: Jul. 20, 1990

[30] Foreign Application Priority Data

Aug. 17, 1989 [AT] Austria ................. 1949/89

[51] Int. Cl.$^5$ ........................................ G01N 33/52
[52] U.S. Cl. ............................. 436/88; 436/164; 436/172
[58] Field of Search ............... 436/86, 87, 88, 165, 436/172, 164

[56] References Cited
U.S. PATENT DOCUMENTS 4,568,647 2/1986 Sanford .................. 436/88

Primary Examiner—James C. Housel
Assistant Examiner—David Redding
Attorney, Agent, or Firm—Hill, Van Santen, Steadman & Simpson

[57] ABSTRACT

An optical method for quantitative determination of human serum albumin (HSA) in biological liquids such as urine is based on the observation that the absorption and fluorescence of certain anionic cyanine dyes possessing a terminal cyano group and having the general formula

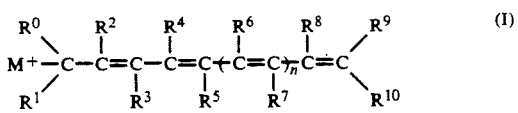

are strongly affected by HSA. This approach is distinctly more sensitive than existing techniques, allowing the detection and quantization of micro-albuminuria (i.e. detection of HSA in the 1–10 mg per liter concentration range) at costs which are distinctly lower than those for existing immunological assays. It is also much more specific for HSA than existing assays based on dye binding. Because the dyes has long wave absorptions and emissions, use can be made of electro-optical components based on semiconductor technology.

6 Claims, 1 Drawing Sheet

METHOD FOR DETECTION AND DETERMINATION OF HUMAN SERUM ALBUMIN

BACKGROUND OF THE INVENTION

1. Field of the Invention

The invention relates to a new fluorimetric method for quantitative determination of human serum albumin (HSA) in biological liquids. The method is based on the observation that the intensity of the fluorescence of certain anionic cyanine dyes is intensified in the presence of human serum albumin and consequently provides an optical parameter for determination of human serum albumin.

2. Description of the Prior Art

Numerous methods for specific determination of albumin in biological liquids have been described in the literature: 1) The enzyme-linked immunosorbent assay (ELISA) is a very sensitive and selective immunological enzimatic method: Bergmeyer, Methods of Enzymatic Analysis, Third Edition, 1986, vol IX, p. 57. Detection of enzyme activity can be by either optical or other methods.

2) The radioimmuno assay (RIA) is a sensitive and selective method: J. Woo, M. Floyd, D. C. Cannon, B. Kahan, Radioimmunoassay for Urinary Albumin, Clin. Chem. 24, 1464–7 (1978).

3) Immunoelectrophesis is a sensitive and selective electrophoretic immunological method (C. B. Laurell, Quantitative Estimation of Protein by Electrophoresis in Agarose Gel Containing Antibodies, Anal. Biochem. 15, 45–52 (1966)).

4) Kinetic methods for determination are based on the intrinsic lipase activity of HSA. In these methods, the cleavage of a synthetic fatty acid ester which acts as an enzyme substrate is photometrically or fluorometrically observed as a function of time: A. R. Gürakar, O. S. Wolfbeis, A Sensitive Kinetic Assay of Serum Albumin Based on its Enzyme Like Hydrolytic Activity, Using a New Chromogenic and Fluorogenic Substrate, Clin. Chim. Acta 172, 35–46 (1988).

5) Finally, there are methods which are based on the spectral variations of dyes that bind to albumin: K. V. Waller, K. M. Ward, J. D. Mahan, D. K. Wismatt, Current Concepts in Proteinuria, Clin. Chem. 35 (5), 755–65 (1989). Among those, the best known is the CBB method: The dye Coomassie Brilliant Blue binds to HSA and changes its color from yellow to blue. This color change is caused by the change of the pK value of the dye following binding to HSA. As a result, the dye is converted into the blue conjugated base form: M. M. Bradford, A Rapid and Sensitive Method for the Quantitation of Microgram Quantities of Protein Utilizing the Principle of Protein-Dye binding, Anal. Biochem. 72, 248–54 (1976).

Disadvantages of the Existing Methods

There are several reasons why the methods known are not completely satisfying Methods based on a spectral change of a dye in the presence of HSA are not very sensitive (detention limit of 10–100 mg/l) and also are not specific which limits the precision of the methods. For an early detection of albuminuria a detection limit of 1 mg/l is desirable.

Electrophoretic methods are time consuming. Additionally, the quantification of the results often turns out to be difficult because in many cases there is no complete separation of HSA from other protein fractions which may cause major errors. Although there are some attempts to improve the technique of separation, e.g. isoelectric focusing (E. Meisinger, N Gretz, M. Strauch, A New Possibility to Analyse Urinary Proteins: Isoelectric Focusing With Immobilized pH Gradients, Nephron 43 (1), 67–9 (1986); immunoelectrophoresis (C. B. Laurell, Quatitative Estimation of Protein by Electrophoresis in Agarose Gel Containing Antibodies, Anal. Biochem. 15, 45–52 (1966), these expensive methods remain restricted to special applications.

Kinetic methods that are based on the intrinsic lipase-activity of HSA are also not very sensitive and selective. A limiting fact is the interference of most protein fractions, specially lipases.

Although state of the art immunological methods appear to be very sensitive and selective, they are expensive and work-intensive. The enzyme-linked immunosorbent assay (the most sophisticated immunological method known so far) requires an incubation time of approximately 210 minutes.

SUMMARY OF THE INVENTION

The present invention provides a new method for determination of HSA that doesn't suffer from the disadvantages mentioned above. Sensitive HSA assay is achieved by means of an appropriate fluorimetric determination of HSA.

The invention is based on the use of anionic cyanine dyes of the general formula (I)

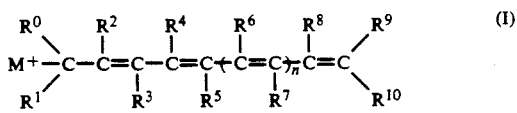

where n is 0 or 1, $M^+$ can be any monovalent cation, $R^0$ is cyano, aryl, or COR (with R standing for alkoxy, alkyl, or aryl), and $R^1$ is cyano, aryl or COR (with R standing for for alkoxy, alkyl, or aryl), $R^2$, $R^8$ stand for hydrogen, alkyl, or cyano, $R^3$, $R^5$, $R^6$, $R^7$ stand for hydrogen and alkyl, $R^4$ stands for hydrogen, halogen, alkyl, aryl, aryloxy, alkoxy, or $NR_2$ (with R standing for alkyl or aryl), $R^9$ stands for cyano, aryl, COR (with R standing for alkoxy, alkyl, or aryl), or CO—NAB (with A standing for alkyl, aryl, or carbamoyl and B standing for alkyl, or aryl), hydrogen, or heterocyclyl, $R^{10}$ stands for cyano, aryl, COR (with R standing for alkoxy, alkyl, or aryl), CO—NAB (with A standing for alkyl, aryl or carbamoyl, and B standing for alkyl, or aryl), hydrogen, or heterocyclyl and where at least one substituent of $R^0$, $R^1$, $R^9$ or $R^{10}$ stands for cyano. $R^3$–$R^5$ can also stand for the members of a ring, e.g. for —$(CH_2)_2$— or $(CH_2)_3$—.

Particularly useful compounds include those where n is 0, $R^2$ and $R^8$ stand for hydrogen, $R^3$–$R^5$ stand for an ethylene or propylene group and $R^4$ stands for chlorine.

Special attention is paid to the compounds of the formula (I) where $R^0$, $R^1$, $R^9$ are cyano and $R^{10}$ stands for cyano or a benzazol-2-yl-substituent such as benzoxazolyl, benzthiazolyl, or their 5-chloro derivatives.

The following table shows a selection of anionic cyanine dyes without, however, thereby limiting the number of the fluorescence dyes suitable for this method. Respective Absorption maxima are listed in the last column.

no such effect produced by other protein fractions of HSA in biological liquids. Gamma-globulines, for example, are the second largest fraction with respect to the excretion amount in most renal diseases. They cause only less than 0.1% of the signal change of an equal amount of HSA. Thus, this method of specific determination of HSA can be applied without preceding separation of HSA from other protein fractions.

TABLE 1

Substitution patterns and absorption maxima (in nm) of typical anionic cyanine dyes of general formula (I), which are applicable to the fluorimetric determination of HSA.

| No. | n | $R^0$ | $R^1$ | $R^2$ | $R^3$-$R^5$ | $R^4$ | $R^6$ | $R^7$ | $R^8$ | $R^9$ | $R^{10}$ | λmax [nm] |
|---|---|---|---|---|---|---|---|---|---|---|---|---|
| 1 | 0 | CN | CN | H | —(CH$_2$)$_2$— | H | — | — | H | CN | CN | 584 |
| 2 | 0 | CN | CN | H | —(CH$_2$)$_2$— | Ph | — | — | H | CN | CN | 594 |
| 3 | 0 | CN | CN | H | —(CH$_2$)$_2$— | OCH$_3$ | — | — | H | CN | CN | 578 |
| 4 | 0 | CN | CN | H | —(CH$_2$)$_2$— | N(CH$_3$)$_2$ | — | — | H | CN | CN | 540 |
| 5 | 0 | CN | CN | H | —(CH$_2$)$_2$— | CH$_3$ | — | — | H | CN | CN | 595 |
| 6 | 0 | CN | CN | H | —(CH$_2$)$_2$— | Cl | — | — | H | CN | CN | 599 |
| 7 | 0 | CN | COOEt | H | —(CH$_2$)$_2$— | Cl | — | — | H | CN | COOH | 608 |
| 8 | 0 | CN | CN | H | —(CH$_2$)$_3$— | OCH$_3$ | — | — | H | CN | CN | 564 |
| 9 | 0 | CN | CN | H | —(CH$_2$)$_3$— | Cl | — | — | H | CN | CN | 580 |
| 10 | 0 | CN | COOEt | H | —(CH$_2$)$_3$— | Cl | — | — | H | CN | COOEt | 588 |
| 11 | 0 | CN | CN | H | —CH$_2$OCH$_2$— | H | — | — | H | CN | CN | 547 |
| 12 | 0 | CN | CN | H | H, H | H | — | — | H | CN | CN | 538 |
| 13 | 0 | CN | CN | H | H, H | Cl | — | — | H | CN | CN | 564 |
| 14 | 0 | CN | CN | CN | H, H | H | — | — | CN | CN | CN | 632 |
| 15 | 0 | CN | CN | CN | —CH==CH— | H | — | — | CN | CN | CN | 574 |
| 16 | 0 | CN | CN | H | H, H | H | — | — | H | CN | COOEt | 542 |
| 17 | 0 | CN | CN | CH$_3$ | H, H | H | — | — | CH$_3$ | CN | CN | 572 |
| 18 | 1 | CN | CN | H | H, H | H | H | H | H | CN | CN | 632 |
| 19 | 0 | CN | CN | H | —(CH$_2$)$_2$— | Cl | — | — | H | CN | 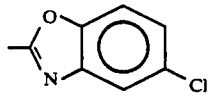 | 648 |
| 20 | 0 | CN | CN | H | —(CH$_2$)$_2$— | Cl | — | — | H | CN | 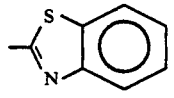 | 658 |
| 21 | 0 | CN | CN | H | —(CH$_2$)$_2$— | Cl | — | — | H | CN | | 627 |
| 22 | 0 | CN | CN | H | —(CH$_2$)$_2$— | Cl | — | — | H | CN | CO—Ph | 597 |
| 23 | 0 | CN | CN | H | —(CH$_2$)$_2$— | Cl | — | — | H | CN | CONHCONH$_2$ | 600 |

The cyanine dyes of the present invention are water-soluble violet, blue, or green compounds. Their fluorescence is orange or red. Fluorescence in aqueous solution is rather weak.

When HSA is added to a solution of one of the dyes of general formula (I), the adsorption and fluorescene maximum is shifted towards longer wavelengths, and fluorescence intensity is considerably enhanced. This effect is very strong. Even very small quantities of HSA cause a remarkable signal change. Surprisingly, there is Due to a linear relationship between excitation energy and fluorescence intensity over a wide range, the signal (and, consequently, the sensitivity of the method) can be highly increased by laser excitation. Additionally, a very good signal to noise ratio can be achieved by making use of the red shift of the excitation maximum of the fluorescent dye upon binding to HSA.

Figure 1:
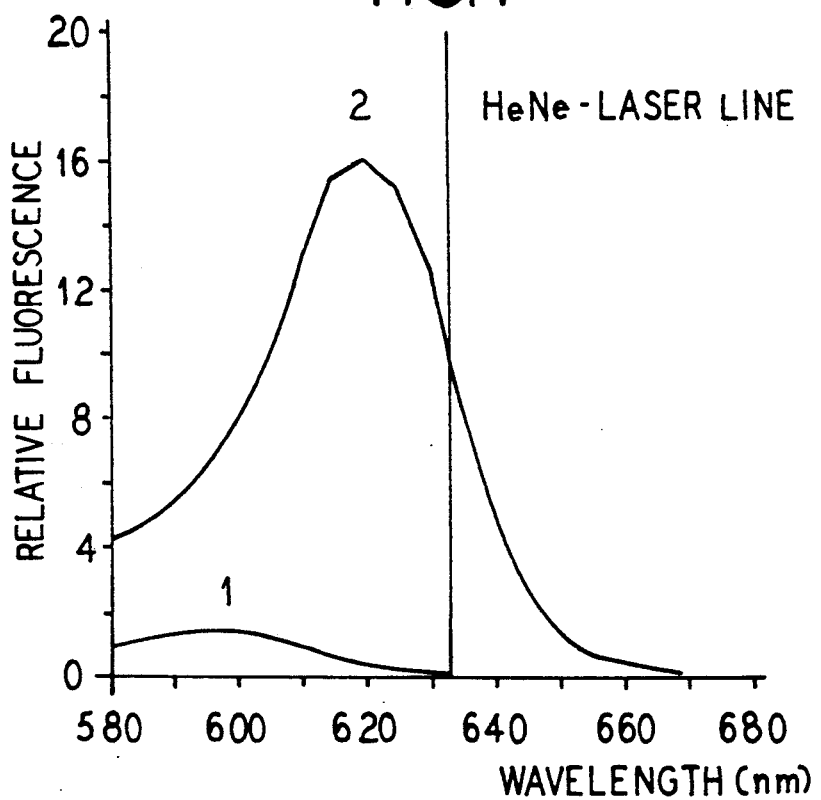
FIG. 1 illustrates the excitation spectra of a typical dye (No.6 in Table 1) in the absence and presence of HSA as were obtained by varying the excitation wavelength but maintaining the emission wavelength constant (640 nm)

Excitation spectra of dye no. 6 of Table 1 (measured at an emission wavelength of 640 nm). In the absence of HSA (curve 1) fluorescence intensity is very low. However, by adding HSA (curve 2), fluorescence intensity is enhanced and the excitation maximum is shifted to longer wavelengths. As can be seen in FIG. 1, when a HeNe-laser is utilized as an excitation source, dye molecules not bound to HSA are only inefficiently excited at 633-nm. Thus, background fluorescence is considerably reduced. Upon binding to HSA, the excitation maximum is longwave shifted so the dye is more efficiently excited by the laser line. As a result, there is a highly selective excitation of the HSA-bound form to a high extent and the background fluorescence of the weakly fluorescing unbound form of the fluorescent dye can practically be neglected.

Other dyes of the general formula (I) can be applied in the same way and, thus, can be, analyzed using conventional sources, e.g. laser diodes (LD) or light emitting diodes (LED).

In this technique, the detection limit of the HSA is limited only by the poor stability and difficult handling of highly diluted, HSA calibration solutions because of adsorption processes on surfaces. Its sensitivity is therefore comparable to, or even better than, the most sensitive methods of the state of the art.

In a further extension of the invention the change of fluorescence depolarization or fluorescence decay time is used as a parameter instead of the change of fluorescence intensity as a result of the binding of the fluorescent dye to HSA. It is observed that the fluorescence of an appropriate fluorescent dye in aqueous solution of pH 7.40 is completely depolarized when bound to HSA. Measurement of polarized fluorescence therefore provides another possibility of qualitative and quantitative detection of HSA. Also, the fluorescence decay time of the fluorescent dye changes when bound to HSA, a fact that provides another method for qualitative and quantitative detection of HSA, using time resolved fluorometry.

In comparison to state-of-the-art methods for determination of HSA, the new method offers some decisive advantages:

1. Because the determination is based on addition of a reagent solution to a sample solution and subsequent measurement of the fluorescence intensity, polarization, or lifetime, both the time requirements and costs of the method can be kept low.

2. The sensitivity of the method can be adjusted to any probe by variation of the concentration of the dye and the instrumental parameters. It also is at least as sensitive as are previously existing methods.

3. The method is very selective. Even a large excess of other protein fractions, such as those ocurring in biological liquids does not interfere. Thus, a separation step is not required.

4. Because of the compatibility of the appropriate fluorescence dye with solidstate optical components such as light emitting diodes or laser diodes (used as excitation sources) and photodiodes (used as detectors), all advantages of semiconductor technology (such as low voltage supply, compactness, low current consumption, high lifetime and reliability) are incorporated.

5. Because of the longwave fluorescence excitation and emission, the potentially interfering shortwave background fluorescence of biological material is excluded. Therefore, full use can be made of the inherent sensitivity of fluorometry.

The appropriate fluorescent dyes are accessible by methods described later here, and by J. L. Slominskii, S. V. Popov, A. Ilchenko, A. I. Tolmachev, Zh. Organ. Khimii, 21, 1294 (1985) as well as M. Strell, W. B. Braunbruck, W. F. Fühler, O. Huber, Liebigs Ann. Chem. 587, 177 (1954).

For preparation of the anionic cyanine dyes of formula (I), derivatives of dialdehydes of formula (II)

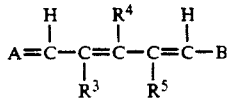

where
A means [$X^- \ ^+N(CH_3)_2$] or oxygen, with $X^-$ standing for an anion (especially perchlorate),
B means —$N(CH_3)_2$, or —$OCH_3$, or —OH, and
$R^3$, $R^4$, $R^5$ have the same meaning as described (formula I). are reacted in presence of a basis condensing agent with active methylene compounds of general formula (III)

where
$R^0$ has the same meaning as described above (formula I),
to give an intermediate of formula (IV) which is isolated:

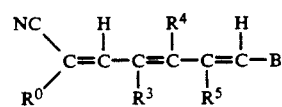

There,
B stands for —$N(CH_3)_2$, —$OCH_3$, or —OH and
$R^0$, $R^3$, $R^4$, $R^5$ have the same meaning as described above (formula I).

In a second step, the intermediate of formula (IV) can be reacted with an additional active methylene component of formula (V)

where
$R^9$, $R^{10}$ have the same meaning as described above (formula I)
to obtain an anionic cyanine dye of formula (I). this reaction also is carried out in the presence of bases.

In case both methylene components (III) and (V) are identical, the isolation of the intermediate products of formula (IV) is unnecessary and the reaction can be carried out as a one pot synthesis.

Suitable catalytic bases include pyridine, tertiary aliphatic amines, and hydroxides of quarternary amines, alkaline and earth alkaline metals. In case of highly active methylene components (e.g. malonodinitrile), the reaction preferably is carried out in pyridine. Less active methylene components are preferably reacted in pyridine/triethylamine mixtures or by using tetramethylammonium hydroxide as a base.

Both reaction steps are preferably carried out in presence of a solvent or diluting agent in the temperature range from 20° to 100° C. Suitable solvents are the above-mentioned liquid organic bases, preferably pyridine. When hydroxides are applied as base components, anhydrous ethanol or methanol are preferred.

In order to avoid reaction of the dialdehyde derivative (II) with two molecules (III) in the first step (which is an undesirable side reaction), an excess of (II) is supplied and component (III), which can be diluted first in one of the above mentioned solvents, is slowly added.

The starting compounds of formula (II) are known: L. Berlin, and O. Riester, in: Houben Weyl, Methoden der organischen Chemie, 4. ed., vol. 5/1d, Georg Thieme Publ., Stuttgart 1972; G. A. Reynolds, and K. H. Drexhage, J. Org. Chem. 42, 885 (1977).

In the following examples, the syntheses of two fluorescent dyes (out of table 1) and their use for determination of HSA in urines is described. However, numerous other modifications of the method are feasible, in particular methods with improved sample preparation such as in autoanalyzers and flow-injection manifolds, in automatted clinical analyzers or disposable probes.

EXAMPLE 1

Synthesis of an HSA-sensitive fluorescent dye (number 6 in table 1) excitable with a helium-neon laser.

5 ml of pyridine are added to a mixture of 6.3 g (20 mmol) N-[(2-chloro-3-(dimethylamino)-methylene)-1-cyclopentene-1-yl]-methylene-N,N-dimethyl-ammonium perchlorate (II) (A: $ClO_4^-$ $+N(CH_3)_2$; B: $N(CH_3)_2$; $R^4$: Cl; $R^3-R^5$: $-(CH_2)_2-$) and 3.3 g (50 mmol) malonodinitrile. The mixture immediately turns to dark blue and soon solidifies to form a crystal cake. The suspension is heated to 70°–80° C. for one hour and finally kept in a refrigerator overnight. Then, 20 ml of diethylether are added and the mixture is filtered. The precipitate is washed with diethylether and dried in a desiccator over $P_4O_{10}$ to remove residual pyridine. Yield: 6.7 g (68%). The dye can be applied in this method for HSA determination without further purification.

EXAMPLE 2

Synthesis of an HSA-sensitive fluorescent dye (No. 19 in table 1 ) excitable with a 670-nm diode laser.

(a) A solution of 1.2 g (18 mmol) malonodinitrile in 5 ml pyridine is added under stirring to a solution of 7.0 g (22.3 mmol) N-[2-chloro-3-(dimethylamino)-methylene]1 -cyclopentene-1-yl]-methylene-N,N-dimethyl-ammonium perchlorate (II) (A: $ClO_4^-$ $+N(CH_3)_2$; B: $N(CH_3)_2$; $R^4$: Cl; $R^3-R^5$: $-(CH_2)_2-$) over a time period of 10 minutes. Then the solution is kept at 70° C. for 15 minutes, and chilled. Upon addition of petrol ether the precipitate obtained is sucked off, washed with a total of 500 ml of methanol/water 1:1 (v/v) to yield 3.6 g of violet needles. For purification, the product is recrystallized from toluene. Mp.: 212° C.

(b) In the second step, 0.16 g (0.69 mmol) of this product and 0.14 g (0.73 mmol) of 5-chloro-2-cyanomethylene-benzoxazole are dissolved under gentle heating in approximately 15 ml of methanol. Then, 0.13 (0.7 mmol) tetramethylammonium hydroxide ($\times 5$ $H_2O$) are added and the solution is stirred at room temperature for another two hours. The suspension thus obtained is treated with 50 ml of diethylether and finally sucked off. The product is washed two times with diethylether. Yield: 0.15 g (49% of theory). Mp.: 221° C. The dye can be applied without further purification, but may be purified by chromatography on silica gel using an acetone/toluene mixture (1:1, v/v) as an eluent.

EXAMPLE 3

Determination of HSA in pathological urine specimens in the presence of various protein fractions, using the dye of example 1 and a 2-m Watt helium-neon laser as the excitation light source.

a) Preparation of the Stock Solution of the Fluorescent Dye

The fluorescent dye of example 1 is dissolved in anhydrous isopropanol. In order to make this stock solution stable, the concentration of the dye is adjusted to an absorbance of about 1.5 per 1 cm at 599 nm. The solution has to be stored in the dark.

b) Buffer

Figure 2:
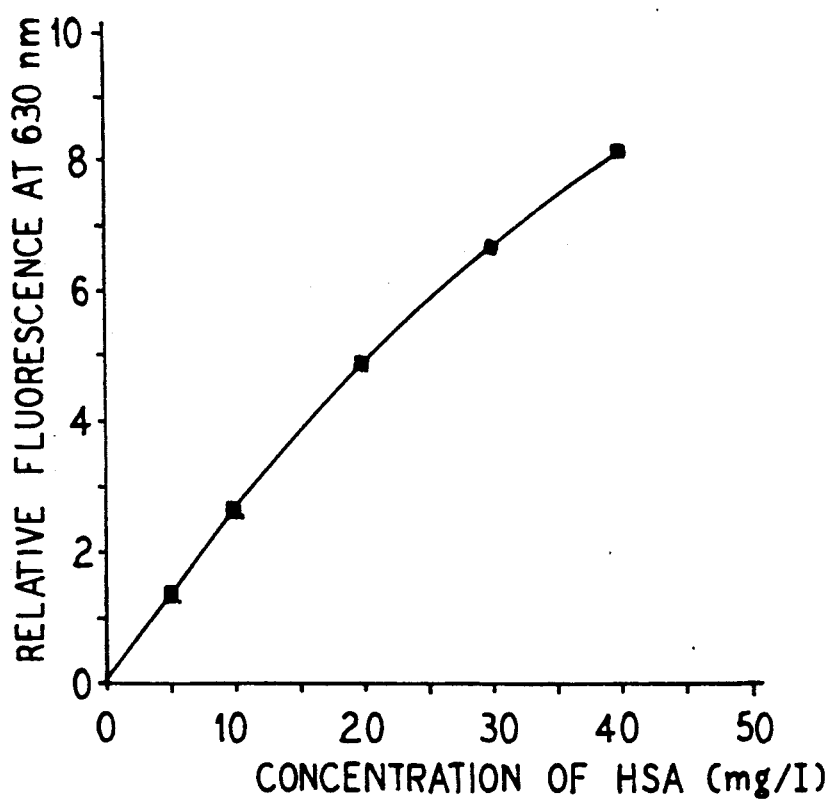
FIG. 2 is a graphic illustration of HSA concentration with respect to measured fluorescence intensity which illustrates the detection limit to be as 0-1 mg HSA per liter and the dynamic range of the assay to be from 0 to above 40 mg per liter.

Phosphate buffer pH = 7.40, adjusted to physiological ionic strength (I = 160 mmol) with NaCl.

c) HSA Calibration Stock 10 mg of lyophilized HSa are dissolved in 100 ml buffer.

d) Establishing the Calibration Curve 0.0, 0.5, 1, 2, 3, and 4 ml of the HSA calibration stock are filled up with buffer to a final volume of 9.5 ml 0.5 ml of the dye stock solution are added to each solution. After mixing, the solutions are immediately measured in the fluorometer under helium-neon laser excitation. The analytical signal used is the fluorescence intensity at 630- nm (so-called anti-Stokes fluorescence). The calibration curve obtained in this way is shown in FIG. 2. Its range is from 0 to 40 mg/l HSA.

e) Determination of HSA in Urine

The determination of HSA in urine is carried out by analogy to the above method for the calibration curve. It is important to ensure that urines having sediments or displaying turbidity are filtered or centrifuged prior to analysis. The amount of urine used for the determination mainly depends on the respective content of HSA. Dilution must be accomplished in a way that the respective value lies within the range of the calibration curve (0–40 mg/l HSA).

Results

The following is a selection of results obtained in HSA-determinations of some urine specimens, and a comparison with data obtained by the immuno-nephelometric and immuno-tubidimetric methods:

Urine 1: Very turbid, highly pathological urine; accompanying proteins: Bence-Jones 3200 mg/l; HSA by this method: 60 mg/l; immuno-nephelometric method: 65 mg/l.

Urine 2: Clear urine, slight microalbuminuria detectable; HSA by this method: 30 mg/l; immuno-nephelometric method: 32.5 mg/l.

Urine 3: Contains sediments, no pathological albuminuria detectable. HSA by this method: 18 mg/l; immuno-nephelometric method: 15.5 mg/l.

Urine 4: Clear urine, no pathological albuminuria detectable; HSA via this method: 10 mg/l; turbidimetric method: HSA below detection limit Urine 5: Clear urine, higly pathological (albuminuria); accompanying proteins: globulines; HSA by this method: 3100 mg/l; immuno-nephelometric method: 3025 mg/l.

Urine 6: Synthetic urine standard containing 59 mg/l gamma-globulin; HSA via this method: 0 mg/l.

We claim:

1. A method for optical detection and quantitative determination of human serum albumin or HSA in biological liquids comprising the steps of
   a) providing a sample of a biological liquid containing human serum albumin or HSA;
   b) adding to the sample an anionic cyanine dye of general formula (1)

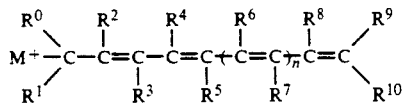

where
n means 0 or 1;
$M^+$ is any monovalent cation;
$R^0$ is cyano, aryl, or COR where R stands for alkoxy, alkyl or aryl;
$R^1$ is cyano, aryl, or COR where R stands for alkoxy, alkyl, or aryl;
$R^2$, $R^8$ each stand for hydrogen, alkyl, or cyano;
$R^3$, $R^5$, $R^6$, $R^7$ each stand for hydrogen or alkyl;
$R^4$ stands for hydrogen, halogen, alkyl, aryl, aryloxy, alkoxy, or $NR_2$ where R stands for alkyl or aryl;
$R^9$ stands for cyano, aryl, COR where R stands for alkoxy, alkyl, or aryl, CO-NAB where A stands for alkyl, aryl, or carbamoyl and B stands for alkyl or aryl, hydrogen, or heterocyclyl;
$R^{10}$ stands for cyano, aryl, COR where R stands for alkoxy, alkyl, or aryl, CO-NAB where A stands for alkyl, aryl or carbamoyl, and B stands for alkyl or aryl, hydrogen, or heterocyclyl;
and where at least one substituent of $R^0$, $R^1$, $R^9$ or $R^{10}$ stands for cyano;

c) measuring the increase in fluorescence intensity, or the change in fluorescence polarization, or the change in fluorescence lifetime of the dye, or the change in absorption of the dye as a result of binding of HSA to the dye; and d) relating the change in fluorescence or absorption to the actual amount of HSA in the sample.

2. A method of claim 1, wherein
n is O,
$R^2$, $R^8$ each stand for hydrogen,
$R^3$ and $R^5$ each stand for an ethylene or propylene bridge,
$R^4$ stands for chlorine,
$R^0$, $R^1$, $R^9$ each stand for cyano, and
$R^{10}$ stands for cyano, or a substituted 2-benzoxazolyl group.

3. A method according to claim 1 wherein a helium-neon laser or a laser diode is used as the excitation light source in step c).

4. A method according to claim 1 prior to the step a) wherein the sample is first filuted or injected into a carrier stream.

5. The method of claim 1, wherein $R^3$ and $R^5$ each stand for $(CH_2)_2$.

6. The method of claim 1, wherein $R^3$ and $R^5$ each stand for $(CH_2)_3$.

* * * * *